(12) United States Patent
Garai et al.

(10) Patent No.: US 12,714,335 B2
(45) Date of Patent: Aug. 25, 2026

(54) GLUCOSE SENSOR BASED ON OPEN CIRCUIT POTENTIAL (OCP) SIGNAL

(71) Applicant: Medtronic MiniMed, Inc., Northridge, CA (US)

(72) Inventors: Ellis Garai, Northridge, CA (US); Sarkis D. Aroyan, Northridge, CA (US); Anuj M. Patel, Northridge, CA (US); Michael E. Miller, Northridge, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 72 days.

(21) Appl. No.: 17/474,921

(22) Filed: Sep. 14, 2021

(65) Prior Publication Data

US 2023/0080129 A1 Mar. 16, 2023

(51) Int. Cl.
*A61B 5/00* (2006.01)
*A61B 5/145* (2006.01)
*A61B 5/1486* (2006.01)

(52) U.S. Cl.
CPC ...... *A61B 5/14532* (2013.01); *A61B 5/14865* (2013.01); *A61B 5/6849* (2013.01)

(58) Field of Classification Search
CPC ............ A61B 5/14532; A61B 5/14865; A61B 5/6849
See application file for complete search history.

(56) References Cited

U.S. PATENT DOCUMENTS

2008/0103356 A1* 5/2008 Minai ................ A61B 1/00016 600/103
2008/0156661 A1* 7/2008 Cooper ................ A61B 5/6848 204/412
2012/0088996 A1 4/2012 Cooper et al.
2012/0172747 A1* 7/2012 Fukuda .................. A61B 5/107 600/547

(Continued)

OTHER PUBLICATIONS

Inyoung, L. et al., "Development of a Third-generation Glucose Sensor Based on the Open Circuit Potential for Continuous Glucose Monitoring," Biosensors Bioelectronics, 2019, vol. 124-125, pp. 216-223.

*Primary Examiner* — Alex M Valvis
*Assistant Examiner* — Grace L Rozanski
(74) *Attorney, Agent, or Firm* — Weaver Austin Villeneuve & Sampson LLP

(57) ABSTRACT

A device for determining a glucose level of a patient includes a set of electrodes comprising a first working electrode, a second working electrode, a counter electrode, and a reference electrode. The reference electrode is electrically coupled to the counter electrode. The device further includes a memory and one or more processors implemented in circuitry and in communication with the memory. The one or more processors configured to determine a sensor signal based on current flowing between the first working electrode and the counter electrode and determine an open circuit potential (OCP) signal based on a voltage across the second working electrode and the reference electrode. The one or more processors are further configured to determine the glucose level of the patient based on the sensor signal and the OCP signal and output an indication of the glucose level.

19 Claims, 8 Drawing Sheets

(56) References Cited

U.S. PATENT DOCUMENTS

| | | | | |
|---|---|---|---|---|
| 2014/0135605 | A1* | 5/2014 | Gottlieb | A61B 5/1486 600/347 |
| 2016/0249840 | A1* | 9/2016 | Pesantez | A61B 5/14865 205/778 |
| 2018/0318834 | A1* | 11/2018 | Fomina | B01L 3/502715 |
| 2019/0076070 | A1* | 3/2019 | Nogueira | G06N 5/022 |
| 2019/0175082 | A1* | 6/2019 | Varsavsky | A61B 5/1468 |
| 2019/0360018 | A1 | 11/2019 | Sode et al. | |
| 2021/0033560 | A1* | 2/2021 | Huang | A61B 5/14735 |

* cited by examiner

GLUCOSE SENSOR BASED ON OPEN CIRCUIT POTENTIAL (OCP) SIGNAL

TECHNICAL FIELD

This disclosure relates to glucose sensors.

BACKGROUND

Glucose sensors are configured to detect and/or quantify the amount of glucose in a patient's body (e.g., interstitial glucose or possibly blood glucose), which enables patients and medical personnel to monitor physiological conditions within the patient's body. In some examples, it may be beneficial to monitor glucose levels on a continuing basis (e.g., in a diabetic patient). Thus, glucose sensors have been developed for use in obtaining an indication of glucose levels in a diabetic patient. Such indications are useful in monitoring and/or adjusting a treatment regimen, which typically includes administration of insulin to the patient.

A patient can measure their glucose using a glucose measurement device (i.e., glucose meter), such as a test strip meter. A continuous glucose measurement system (or a continuous glucose monitor (CGM)) may be configured to determine interstitial glucose; although possible for CGM to determine a glucose level. A hospital hemacue may also be used to determine glucose level. CGMs may be beneficial for patients who desire to take more frequent glucose measurements. Some example CGM systems include subcutaneous (or short-term) sensors and implantable (or long-term) sensors.

SUMMARY

In general, this disclosure describes techniques for configuring a glucose sensor (e.g., a continuous glucose monitor or "CGM") to determine a glucose level (e.g., interstitial glucose level or possibly blood glucose level) based on an open circuit potential (OCP) signal. The OCP signal may refer to a voltage between a working electrode and a reference electrode with little or no current flowing from the working electrode. In some examples, the OCP signal may be generated by setting the working electrode to a high impedance mode. In this way, techniques described herein may help to account for a change in a concentration of oxygen in a tissue of a patient based on the OCP signal to improve an accuracy of an estimation of a glucose level of the patient. In some examples, the glucose level measured by the glucose sensor may be an interstitial glucose level. In such examples, a processor may be configured to convert the interstitial glucose level to a blood glucose level (e.g., such as by scaling and offsetting).

In one example, a device for determining a glucose level of a patient includes a set of electrodes, a memory, and one or more processors. The a set of electrodes comprise a first working electrode, a second working electrode, a counter electrode, and a reference electrode. The reference electrode is electrically coupled to the counter electrode. The one or more processors are implemented in circuitry and in communication with the memory. The one or more processors configured to determine a sensor signal based on current flowing between the first working electrode and the counter electrode and determine an open circuit potential (OCP) signal based on a voltage across the second working electrode and the reference electrode. The one or more processors are further configured to determine the glucose level of the patient based on the sensor signal and the OCP signal and output an indication of the glucose level.

In another example, a method for determining a glucose level of a patient includes determining, with one or more processors, a sensor signal based on current flowing between a first working electrode and a counter electrode and determining, with one or more processors, an open circuit potential (OCP) signal based on a voltage across a second working electrode and a reference electrode. The reference electrode is electrically coupled to the counter electrode. The method further includes determining, with the one or more processors, the glucose level of the patient based on the sensor signal and the OCP signal and outputting, with the one or more processors, an indication of the glucose level.

In one example, a non-transitory computer-readable storage medium has stored thereon instructions that, when executed, configure one or more processors to determine a sensor signal based on current flowing between a first working electrode and a counter electrode and determine an open circuit potential (OCP) signal based on a voltage across a second working electrode and a reference electrode. The reference electrode is electrically coupled to the counter electrode. The instructions further cause the one or more processors to determine the glucose level of the patient based on the sensor signal and the OCP signal and output an indication of the glucose level.

The details of one or more examples are set forth in the accompanying drawings and the description below. Other features, objects, and advantages will be apparent from the description and drawings, and from the claims.

DETAILED DESCRIPTION

In general, this disclosure describes techniques for configuring a glucose sensor (e.g., a continuous glucose monitor or "CGM") to determine a glucose level based an open circuit potential (OCP) signal. The OCP signal may refer to a voltage between a working electrode and a reference electrode with little or no current flowing from the working electrode. In some examples, the OCP signal may be generated by setting the working electrode to a high impedance mode. In this way, techniques described herein may help to account for a concentration of oxygen (e.g., a change in a concentration or an oxygen level) based on the OCP signal to improve an accuracy of an estimation of a glucose level.

A glucose sensor may be dependent on the presence of oxygen available in the interstitial fluid (ISF). However, the concentration of oxygen in the ISF can vary drastically (e.g., by multiple percentages), and, as a result, can cause variations in the measured glucose signal of the glucose sensor. In accordance with the techniques of the disclosure, the glucose sensor may be configured to measure the impact of fluctuation in oxygen local to the glucose sensor implant site in order to use the fluctuation in oxygen measurement to correct for associated fluctuations in glucose level readings. The glucose sensor may use a secondary electrode that acquires an OCP signal, which may be sensitive to changes in oxygen.

Figure 1:
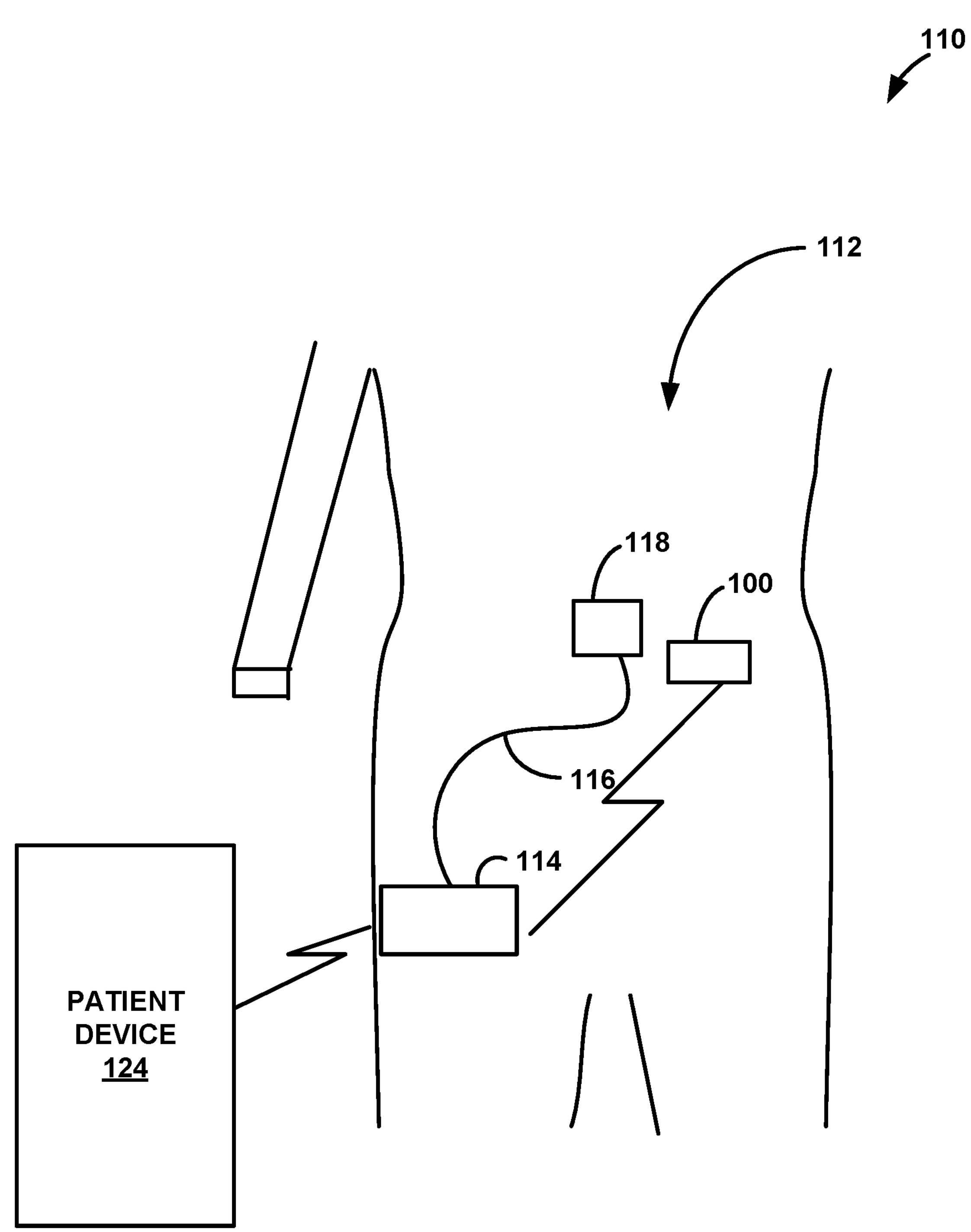
FIG. 1 is a block diagram illustrating an example glucose level management system in accordance with one or more examples described in this disclosure.

FIG. 1 is a block diagram illustrating an example glucose level management system in accordance with one or more examples described in this disclosure. FIG. 1 illustrates system 110 that includes insulin pump 114, tubing 116, infusion set 118, monitoring device 100 (e.g., a glucose level monitoring device comprising a glucose sensor), and patient device 124. Insulin pump 114 may be described as a tethered pump, because tubing 116 tethers insulin pump 114 to infusion set 18. In some examples, rather than utilizing a tethered pump system comprising insulin pump 114, tubing 116, infusion set 118, and/or monitoring device 100, patient 112 may utilize a patch pump. Instead of delivering insulin via tubing and an infusion set, a pump patch may deliver insulin via a cannula extending directly from an insulin pump. In some examples, a glucose sensor may also be integrated into such an insulin pump (e.g., a so-called "all-in-one (AIO) insulin pump").

Patient 112 may be diabetic (e.g., Type 1 diabetic or Type 2 diabetic), and therefore, the glucose level in patient 112 may be controlled with delivery of supplemental insulin. For example, patient 112 may not produce sufficient insulin to control the glucose level or the amount of insulin that patient 112 produces may not be sufficient due to insulin resistance that patient 112 may have developed.

To receive the supplemental insulin, patient 112 may carry insulin pump 114 that couples to tubing 116 for delivery of insulin into patient 112. Infusion set 118 may connect to the skin of patient 112 and include a cannula to deliver insulin into patient 112. Monitoring device 100 may also be coupled to patient 112 to measure glucose level in patient 112. Insulin pump 114, tubing 116, infusion set 118, and monitoring device 100 may together form an insulin pump system. One example of the insulin pump system is the MINIMED™ 670G insulin pump system by MEDTRONIC MINIMED, INC. However, other examples of insulin pump systems may be used and the example techniques should not be considered limited to the MINIMED™ 670G insulin pump system. For example, the techniques described in this disclosure may be utilized with any insulin pump and/or glucose monitoring system that includes an in vivo glucose sensor (e.g., a continuous glucose monitor or other in vivo glucose sensor).

Monitoring device 100 may include a sensor that is inserted under the skin of patient 112 (e.g., in vivo), such as near the stomach of patient 112 or in the arm of patient 112 (e.g., subcutaneous connection). The sensor of monitoring device 100 may be configured to measure the interstitial glucose level, which is the glucose found in the fluid between the cells of patient 112. Monitoring device 100 may be configured to continuously or periodically sample the glucose level and rate of change of the glucose level over time.

In one or more examples, insulin pump 114, monitoring device 100, and/or the various components illustrated in FIG. 1, may together form a closed-loop therapy delivery system. For example, patient 112 may set a target glucose level, usually measured in units of milligrams per deciliter, on insulin pump 114. Insulin pump 114 may receive the current glucose level from monitoring device 100 and, in response, may increase or decrease the amount of insulin delivered to patient 112. For example, if the current glucose level is higher than the target glucose level, insulin pump 114 may increase the insulin. If the current glucose level is lower than the target glucose level, insulin pump 114 may temporarily cease delivery of the insulin. Insulin pump 114 may be considered as an example of an automated insulin delivery (AID) device. Other examples of AID devices may be possible, and the techniques described in this disclosure may be applicable to other AID devices.

Insulin pump 114 and monitoring device 100 may be configured to operate together to mimic some of the ways in which a healthy pancreas works. Insulin pump 114 may be configured to deliver basal dosages, which are small amounts of insulin released continuously throughout the day. There may be times when glucose levels increase, such as due to eating or some other activity that patient 112 undertakes. Insulin pump 114 may be configured to deliver bolus dosages on demand in association with food intake or to correct an undesirably high glucose level (e.g., in the bloodstream). In one or more examples, if the glucose level rises above a target level, then insulin pump 114 may deliver a bolus dosage to address the increase in glucose level. Insulin pump 114 may be configured to compute basal and bolus dosages and deliver the basal and bolus dosages accordingly. For instance, insulin pump 114 may determine the amount of a basal dosage to deliver continuously and then determine the amount of a bolus dosage to deliver to reduce glucose level in response to an increase in glucose level due to eating or some other event.

Accordingly, in some examples, monitoring device 100 may sample glucose levels for determining rate of change in glucose level over time. Monitoring device 100 may output the glucose level to insulin pump 114 (e.g., through a wireless link connection like BLUETOOTH). Insulin pump 114 may compare the glucose level to a target glucose level (e.g., as set by patient 112 or a clinician) and adjust the insulin dosage based on the comparison. In some examples, insulin pump 114 may adjust insulin delivery based on a predicted glucose level (e.g., where glucose level is expected to be in the next 30 minutes).

As described above, patient 112 or a clinician may set one or more target glucose levels on insulin pump 114. There may be various ways in which patient 112 or the clinician may set a target glucose level on insulin pump 114. As one example, patient 112 or the clinician may utilize patient device 124 to communicate with insulin pump 114. Examples of patient device 124 include mobile devices, such as smartphones, tablet computers, laptop computers, and the like. In some examples, patient device 124 may be a special programmer or controller (e.g., a dedicated remote control device) for insulin pump 114. Although FIG. 1 illustrates one patient device 124, in some examples, there may be a plurality of patient devices. For instance, system 110 may include a mobile device and a dedicated wireless controller, each of which is an example of patient device 124. For ease of description only, the example techniques are described with respect to patient device 124 with the understanding that patient device 124 may be one or more patient devices.

Patient device 124 may also be configured to interface with monitoring device 100. As one example, patient device 124 may receive information from monitoring device 100 through insulin pump 114, where insulin pump 114 relays the information between patient device 124 and monitoring device 100. As another example, patient device 124 may receive information (e.g., glucose level or rate of change of glucose level) directly from monitoring device 100 (e.g., through a wireless link).

In one or more examples, patient device 124 may comprise a user interface with which patient 112 or the clinician may control insulin pump 114. For example, patient device 124 may comprise a touchscreen that allows patient 112 or the clinician to enter a target glucose level. Additionally or alternatively, patient device 124 may comprise a display device that outputs the current and/or past glucose level. In some examples, patient device 124 may output notifications to patient 112, such as notifications if the glucose level is too high or too low, as well as notifications regarding any action that patient 112 needs to take.

Monitoring device 100 may comprise configuration information (e.g., one or more correction factors) related to manufacturing the glucose sensor, which may be used to determine a glucose level of patient 112. In accordance with the techniques of the disclosure, configuration information of monitoring device 100 may be set based on one or more electrical parameters measured in vitro. As used herein, in vitro may refer to when sensor(s) of monitoring device 100 are positioned outside of a human subject. In contrast, in vivo may refer to when one or more sensors of monitoring device 100 are at least partially positioned inside of a human patient.

Electrical parameters may include, for example, a voltage (e.g., an OCP signal), an electrical current (e.g., iSig), or an impedance. In general, the electrical current (e.g., a sensor signal) flowing through a first working electrode of a glucose sensor (i.e., a sensor of monitoring device 100) is indicative of the glucose level in the patient's interstitial fluid. OCP signal may refer to a voltage between a working electrode and a reference electrode with little or no current flowing from the working electrode (e.g., "open circuit").

While voltage at the first working electrode that generates the sensor signal (e.g., iSig) may be measured, the voltage at the first working electrode may be different from an OCP signal. For example, current flow of the sensor signal changes the voltage at the first working electrode from an OCP signal. As such, the voltage at the first working electrode while the first working electrode is used to generate the sensor signal may not represent an OCP signal. Instead, monitoring device 100 may use a second working electrode that is not used to generate the sensor signal to determine the OCP signal.

For example, monitoring device 100 may determine a sensor signal based on current flowing between a first working electrode and a counter electrode. In this example, monitoring device 100 may determine an OCP signal based on a voltage across a second working electrode and a reference electrode. Monitoring device 100 may determine a glucose level of the patient based on the sensor signal and the OCP signal. For instance, monitoring device 100 may determine a multiplication factor based on the OCP signal and multiply the multiplication factor with the sensor signal. Monitoring device 100 may output an indication of the glucose level. For example, monitoring device 100 may output an instruction to insulin pump 114. In some examples, monitoring device 100 may output an indication of the glucose level to patient device 124. Patient device 124 may display the glucose level. For instance, patient device 124 may display the glucose level and patient 112 or caretaker may dispense insulin to patient 112 (e.g., when insulin pump 114 is omitted or bypassed).

Techniques described herein may use an OCP signal to account for a change in oxygen level in the tissue of patient 112, which may add error to the sensor signal. In this way, monitoring device 100 may be calibrated to help to account for a change in oxygen level in the tissue of patient 112, which may improve an accuracy of the glucose device. A more optimal configuration of monitoring device 100 may also improve the longevity of monitoring device 100.

Figure 2:
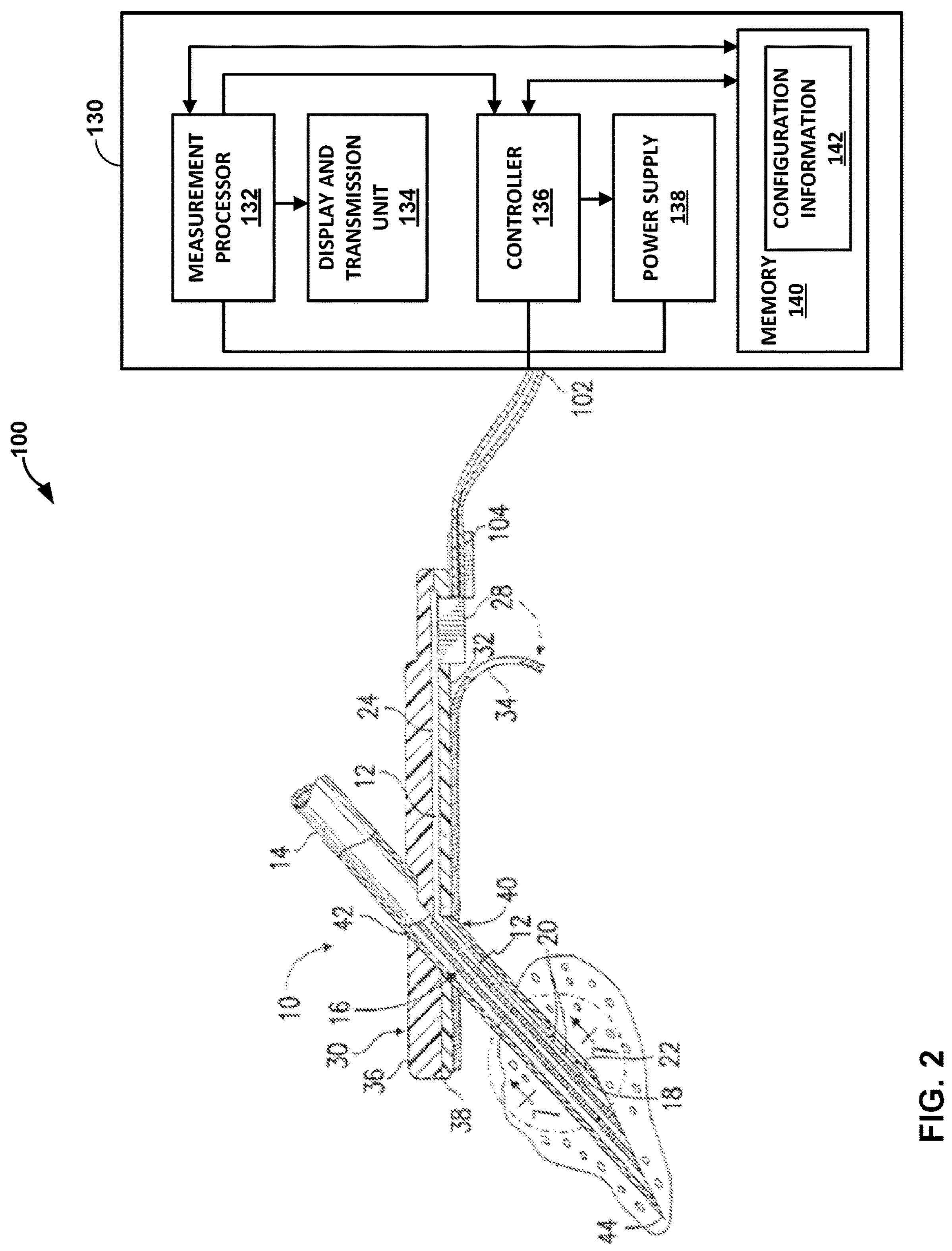
FIG. 2 is a block diagram illustrating an example glucose sensor in accordance with one or more examples described in this disclosure.

FIG. 2 is a block diagram illustrating monitoring device 100 in more detail. In particular, FIG. 2 is a perspective view of a subcutaneous sensor insertion set and a block diagram of sensor electronics device 130 of monitoring device 100 according to an example of the disclosure. As illustrated in FIG. 2, subcutaneous sensor set 10 is provided for subcutaneous placement of an active portion of flexible glucose sensor 12 at a selected site in the body of patient 112. The subcutaneous or percutaneous portion of sensor set 10 includes a hollow, slotted insertion needle 14, and cannula 16. Needle 14 is used to facilitate quick and easy subcutaneous placement of cannula 16 at the subcutaneous insertion site. Inside cannula 16 is glucose sensing portion 18 of glucose sensor 12, which is configured to expose one or more glucose sensor electrodes 20 to the bodily fluids (e.g., blood or interstitial fluid) of patient 112 through window 22 formed in cannula 16. In one example, one or more glucose sensor electrodes 20 may include a counter electrode, a reference electrode, and one or more working electrodes (e.g., a first working electrode and a second working electrode). Examples of the counter electrode, reference electrode, and working electrode(s) are described in more detail with respect to FIG. 3. After insertion, insertion needle 14 is withdrawn to leave cannula 16 with glucose sensing portion 18 and glucose sensor electrodes 20 in place at the selected insertion site.

In particular examples, subcutaneous sensor set 10 facilitates accurate placement of flexible thin film electrochemical glucose sensor 12 of the type used for monitoring specific glucose parameters representative of a condition of patient 112. Glucose sensor 12 monitors glucose levels in the body, and may be used in conjunction with automated or semi-automated medication infusion pumps of the external or implantable type as described above to control delivery of insulin to patient 112.

Particular examples of flexible electrochemical glucose sensor 12 are constructed in accordance with thin film mask techniques to include elongated thin film conductors embedded or encased between layers of a selected insulative material such as polyimide film or sheet, and membranes. Glucose sensor electrodes 20 at a tip end of glucose sensing portion 18 are exposed through one of the insulative layers for direct contact with patient blood or other body fluids, when glucose sensing portion 18 (or active portion) of glucose sensor 12 is subcutaneously placed at an insertion site. Glucose sensing portion 18 is joined to connection portion 24 that terminates in conductive contact pads, or the like, which are also exposed through one of the insulative layers. In other examples, other types of implantable sensors, such as chemical based, optical based, or the like, may be used.

Connection portion 24 and the contact pads are generally adapted for a direct wired electrical connection to a suitable monitor or sensor electronics device 130 for monitoring a condition of patient 112 in response to signals derived from glucose sensor electrodes 20. Connection portion 24 may be conveniently connected electrically to the monitor or sensor electronics device 130 or by connector block 28. Thus, in accordance with examples of the disclosure, subcutaneous sensor sets 10 may be configured or formed to work with either a wired or a wireless characteristic monitor system.

Glucose sensor electrodes 20 may be used in a variety of sensing applications and may be configured in a variety of ways. For example, glucose sensor electrodes 20 may be used in physiological parameter sensing applications in which some type of biomolecule is used as a catalytic agent. For example, glucose sensor electrodes 20 may be used in a glucose and oxygen sensor having a glucose oxidase (GOx) enzyme catalyzing a reaction with glucose sensor electrodes 20. Glucose sensor electrodes 20, along with a biomolecule or some other catalytic agent, may be placed in a human body in a vascular or non-vascular environment. For example, glucose sensor electrodes 20 and biomolecules may be placed in a vein and be subjected to a blood stream, or may be placed in a subcutaneous or peritoneal region of the human body.

Sensor electronics device 130 may include measurement processor 132, display and transmission unit 134, controller 136, power supply 138, and memory 140. Sensor electronics device 130 may be coupled to the sensor set 10 by cable 102 through a connector that is electrically coupled to connector block 28 of connection portion 24. In other examples, the cable may be omitted and sensor electronics device 130 may include an appropriate connector for direct connection to connection portion 104 of sensor set 10. Sensor set 10 may be modified to have connector portion 104 positioned at a different location, e.g., on top of the sensor set to facilitate placement of sensor electronics device 130 over the sensor set.

In examples of the disclosure, measurement processor 132, display and transmission unit 134, and controller 136 may be formed as separate semiconductor chips. However, other examples may combine measurement processor 132, display and transmission unit 134, and controller 136 into a single or multiple customized semiconductor chips. In general, measurement processor 132 may be configured to receive a current and/or voltage from glucose sensor electrodes 20. Glucose sensor electrodes 20 may generate a sensor signal indicative of a concentration of a physiological characteristic being measured. For example, the sensor signal may be indicative of a glucose reading. The sensor signal may be measured at a working electrode (e.g., a first working electrode) of glucose sensor electrodes 20. In an example of the disclosure, the sensor signal may be an electrical current (e.g., iSig) measured at the first working electrode. In another example of the disclosure, the sensor signal may be a voltage (e.g., Vcounter) measured at the working electrode of glucose sensor electrodes 20. Electrical parameters, such as voltage, electrical current, and impedance, may be measured in vitro and may be referred to herein as “in vitro features.”

An example of an impedance parameter may include electrochemical impedance spectroscopy (EIS). EIS may provide additional information in the form of sensor impedance and impedance-related parameters at different frequencies. Moreover, for certain ranges of frequencies, impedance and/or impedance-related data are substantially glucose independent. Such glucose independence enables the use of a variety of EIS-based markers or indicators for not only producing a robust, highly-reliable sensor glucose value (through fusion methodologies), but also assessing the condition, health, age, and efficiency of individual electrode(s) and of the overall sensor substantially independently of the glucose-dependent Isig.

For example, analysis of the glucose-independent impedance data provides information on the efficiency of a sensor of monitoring device 100 with respect to how quickly it hydrates and is ready for data acquisition using, e.g., values for 1 kHz real-impedance, 1 kHz imaginary impedance, and Nyquist Slope (to be described in more detail hereinbelow). Moreover, glucose-independent impedance data provides information on potential occlusion(s) that may exist on the sensor membrane surface, which occlusion(s) may temporarily block passage of glucose into the sensor and thus cause the signal to dip (using, e.g., values for 1 kHz real impedance). In addition, glucose-independent impedance data provides information on loss of sensor sensitivity during extended wear-potentially due to local oxygen deficit at the insertion site-using, e.g., values for phase angle and/or imaginary impedance at 1 kHz and higher frequencies.

Within the context of electrode redundancy and EIS, a fusion algorithm may be used to take the diagnostic information provided by EIS for each redundant electrode (e.g., in systems with multiple working electrodes) and assess the reliability of each electrode independently. Weights, which are a measure of reliability, may then be added for each independent signal, and a single fused signal may be calculated that can be used to generate sensor glucose values as seen by the patient/subject.

The combined use of redundancy, sensor diagnostics using EIS, and EIS-based fusion algorithms may allow for an overall CGM system that is more reliable than systems that do not use EIS. Redundancy is advantageous in at least two respects. First, redundancy removes the risk of a single point of failure by providing multiple signals. Second, providing multiple (working) electrodes where a single electrode may be sufficient allows the output of the redundant electrode to be used as a check against the primary electrode, thereby reducing, and perhaps eliminating, the need for frequent calibrations. In addition, EIS diagnostics may scrutinize the health of each electrode autonomously without the need for a reference glucose value (finger stick), thereby reducing the number of reference values required. However, the use of EIS technology and EIS diagnostic methods is not limited to redundant systems, e.g., those having more than one working electrode. Rather, EIS may be advantageously used in connection with single- and/or multiple-electrode sensors of monitoring device 100.

Measurement processor 132 receives the sensor signal (e.g., a measured current or voltage) after the sensor signal is measured at glucose sensor electrodes 20 (e.g., the first working electrode). Measurement processor 132 may receive the sensor signal and calibrate the sensor signal utilizing reference values. In an example of the disclosure, the reference values are stored in a reference memory (e.g., memory 140) and provided to measurement processor 132. Based on the sensor signals and the reference values, measurement processor 132 may determine a glucose measurement. In accordance with the techniques of the disclosure, measurement processor 132 may further determine the glucose measurement based on an OCP signal. Measurement processor 132 store the glucose measurements in memory 140. The sensor measurements may be sent to display and transmission unit 134 to be either displayed on a display in a housing of monitoring device 100 or transmitted to an external device.

Memory 140 may be any type of memory device and may be configured to store glucose measurements produced by measurement processor 132, reference values used to determine glucose measurements from sensor signals, or other data used and/or produced by measurement processor 132 and/or controller 136. In some examples, memory 140 may further store software and/or firmware that is executable by measurement processor 132 and/or controller 136. As will be explained in more detail below, memory 140 may further configuration information 142. Configuration information 142 may include data that may be executed by controller 136 to configure sensor electronics device 130.

Sensor electronics device 130 may be a monitor which includes a display to display physiological characteristics readings. Sensor electronics device 130 may also be installed in a desktop computer, a pager, a television including communications capabilities, a laptop computer, a server, a network computer, a personal digital assistant (PDA), a portable telephone including computer functions, an infusion pump including a display, a glucose sensor including a display, and/or a combination infusion pump/glucose sensor. Sensor electronics device 130 may be housed in a mobile phone, a network device, a home network device, or an appliance connected to a home network.

Power supply 138 may be a battery. The battery can include three series silver oxide 357 battery cells. In other examples, different battery chemistries may be utilized, such as lithium based chemistries, alkaline batteries, nickel metalhydride, or the like, and a different number of batteries may be used. Sensor electronics device 130 provides power to the sensor set 10 via power supply 138 through cable 102 and cable connector 104.

Controller 136 may be a processor, digital signal processors (DSPs), application specific integrated circuits (ASICs), field programmable gate arrays (FPGAs), or any other equivalent integrated or discrete logic circuitry. In some examples controller 136 may be configured to execute software program code and/or firmware that causes power supply 138 to supply a specific voltage or current to glucose sensor electrodes 20. Glucose sensor electrodes 20 may receive the voltage level or value. In an example of the disclosure, a counter electrode of glucose sensor electrodes 20 may receive the reference voltage from power supply 138. The application of the voltage level causes glucose sensor electrodes 20 to create a sensor signal (e.g., a current through a working electrode) indicative of a concentration of a physiological characteristic being measured (e.g., blood glucose).

Figure 3:
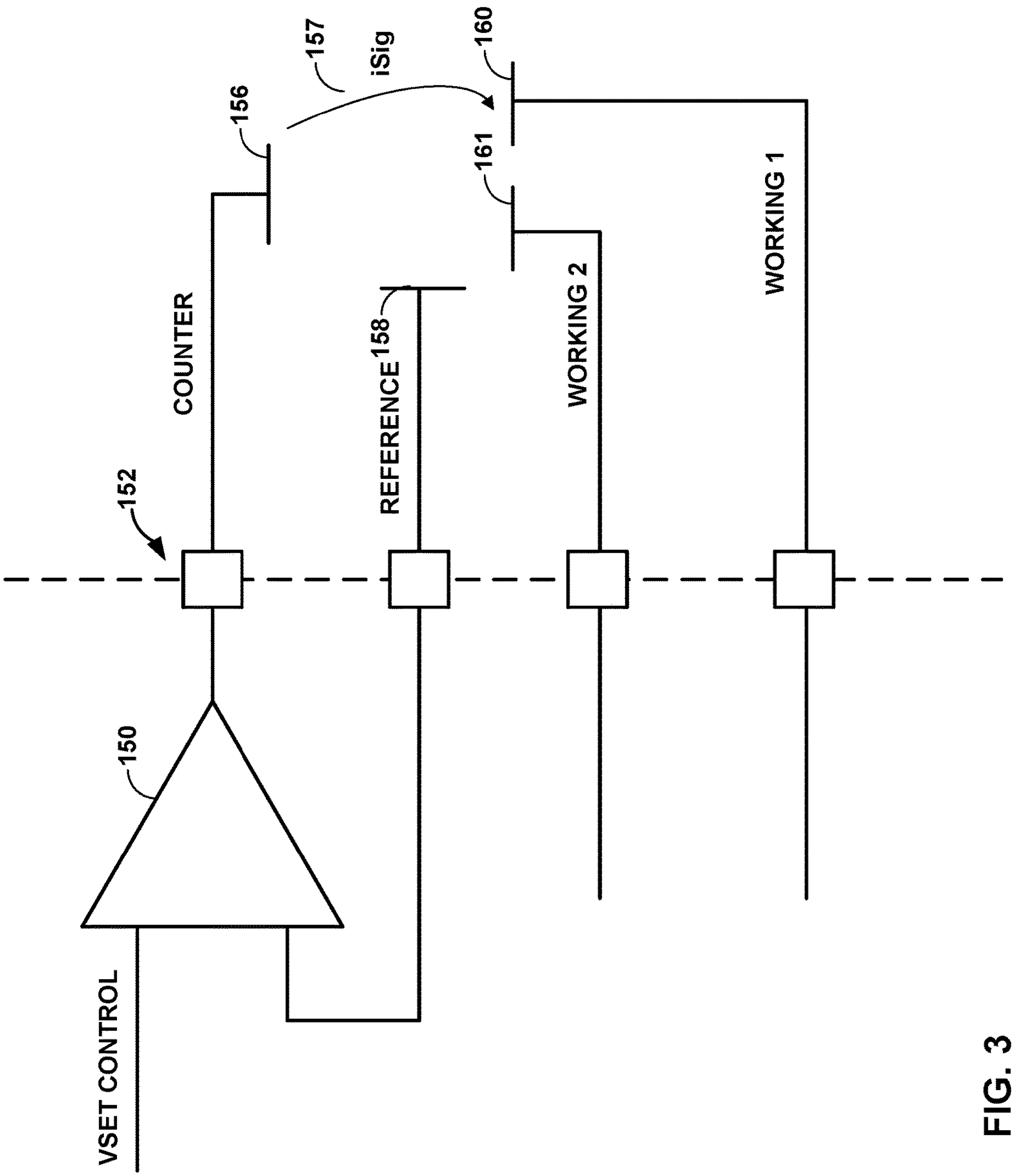
FIG. 3 is a block diagram illustrating example sensor electrodes and a voltage being applied to the sensor electrodes according to an example of the disclosure.

FIG. 3 is a block diagram illustrating example sensor electrodes and a voltage being applied to the sensor electrodes according to an example of the disclosure. In the example in FIG. 3, an operational amplifier (op amp) 150 or other servo controlled device may connect to counter electrode 156, reference electrode 158, working electrode 160, and working electrode 161 (collectively, electrodes 156, 158, 160, 161), through a circuit/electrode interface 152. Op amp 150, utilizing feedback through reference electrode 158, attempts to maintain a prescribed voltage between reference electrode 158 and a working electrode 160 (e.g., VSET) by adjusting the voltage at counter electrode 156. In some examples, the voltage at reference electrode 158 is 850 millivolts (my).

Current 157 (iSig) may then flow from a counter electrode 156 to a working electrode 160. Counter electrode 156 balances the chemical reaction that is occurring at working electrode 160. Measurement processor 132 of FIG. 2 may measure current 157 to determine the electrochemical reaction between glucose sensor electrodes 20 and a biomolecule of a sensor that has been placed in the vicinity of the sensor electrodes and used as a catalyzing agent. The circuitry disclosed in FIG. 3 may be utilized in a long-term or implantable sensor or may be utilized in a short-term or subcutaneous sensor.

Returning to FIG. 2, as discussed above, monitoring device 100 may determine a glucose level for patient 112 based on current 157. In accordance with the techniques of the disclosure, monitoring device 100 may determine the glucose level further based on an OCP signal. Monitoring device 100 may determine the OCP signal based on a voltage across electrodes 20 (e.g., working electrode 161 and reference electrode 158 and/or working electrode 160 and reference electrode 158 of FIG. 3). An OCP signal may refer to a voltage when current flow is zero, either by disconnecting counter electrode 156 (or by placing a very high impedance resistor in the path between working electrodes 160, 161) as to prevent current passage. The OCP signal may represent a potential difference between one or more of working electrodes 160, 161 and reference electrode 158.

In OCP mode, the potentiostat can be used as a simple voltmeter. For example, monitoring device 100 may calculate Equation 1.

$$E_{OCP}=E_{WKG}-E_{REF} \quad \text{EQUATION 1}$$

where $E_{OCP}$ is the OCP signal, $E_{WKG}$ is a voltage at working electrode 161 while working electrode 161 is operating with little or no current and $E_{REF}$ is a voltage at reference electrode 158. While this example uses working electrode 161 to measure $E_{WKG}$, in some examples, working electrode 160 may be used to measure $E_{WKG}$. For example, the processor has shut off a current source and/or increased a supply resistance.

The OCP signal may change with an amount of oxygen in tissue of patient 112. For instance, a voltage of the OCP signal may be correlated (e.g., negatively correlated) with the amount of oxygen in tissue of patient 112. Additionally, oxygen in tissue of patient 112 may add error to a glucose level determined by monitoring device 100. In this way, monitoring device 100 or another device may "correct" errors in a determination of the glucose level from at least an amount of oxygen in tissue of patient 112 using the OCP signal as an estimate of oxygen in tissue of patient 112. As such, monitoring device 100 may help to mitigate or eliminate error caused by a change in oxygen in tissue of patient 112, which may improve an accuracy of monitoring device 100. A more optimal configuration of monitoring device 100 may also improve the longevity of monitoring device 100.

Figure 4:
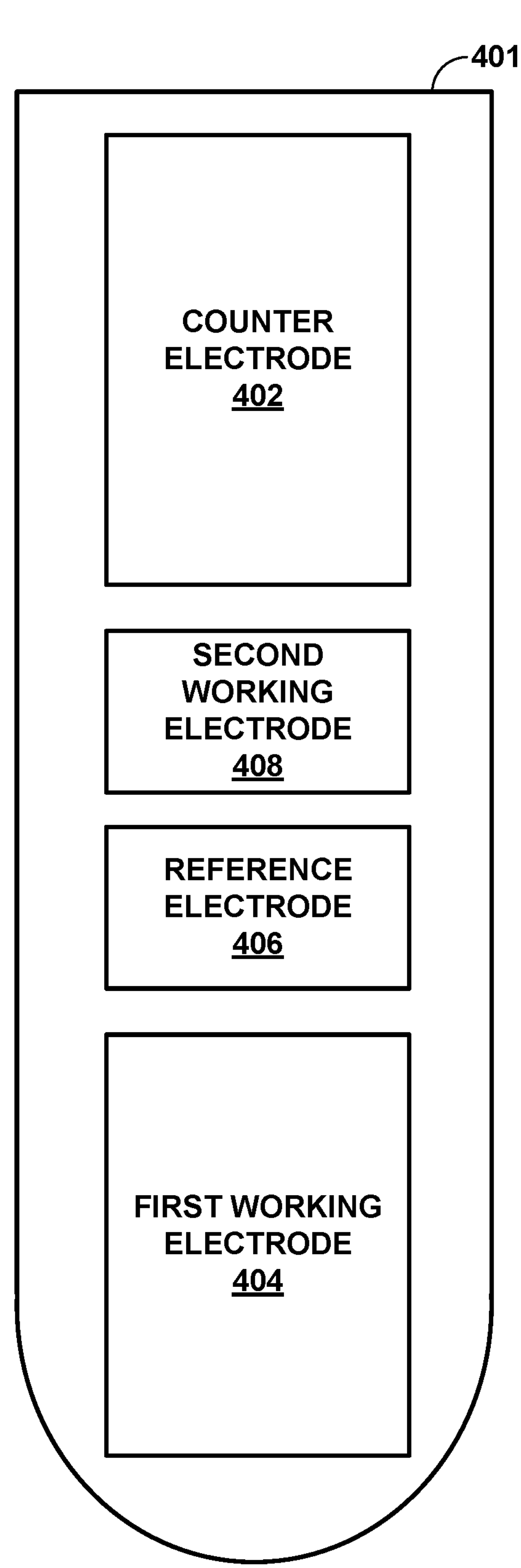
FIG. 4 is a block diagram illustrating an example sensor flex in accordance with one or more examples described in this disclosure.

FIG. 4 is a block diagram illustrating an example sensor flex 401 in accordance with one or more examples described in this disclosure. In some examples sensor flex 401 may represent a single implantable sensor flex.

In the example of FIG. 4, first working electrode 404, second working electrode 408, counter electrode 402, and reference electrode 406 are arranged on a sensor flex 401. In some examples, first working electrode 404, second working electrode 408, counter electrode 402, and reference electrode 406 may be arranged on more than one sensor flex and/or may be arranged in a different order than illustrated in FIG. 4. First working electrode 404 may be configured with an glucose oxidase (GOx) enzyme. In some examples, second working electrode 408 may omit the glucose oxidase (GOx) enzyme.

Monitoring device 100 may be configured to operate first working electrode 404 in a low-impedance mode. When first working electrode 404 is operating in the low-impedance mode, a resistance between first working electrode 404 and counter electrode 402 may be less than a first threshold value. Monitoring device 100 may be configured to operate second working electrode 408 in a high-impedance mode. When second working electrode 408 is operating in the high-impedance mode, a resistance between second working electrode 408 and both counter electrode 402 and reference electrode 406 may be greater than a second threshold value. In this example, the second threshold value may be greater than the first threshold value.

In this way, monitoring device 100 may use first working electrode 404 and counter electrode 402 to generate a sensor signal (e.g., iSig) for determining a glucose level of patient 112 using the relatively "low" resistance between first working electrode 404 and counter electrode 402, which may help to increase an accuracy of the sensor signal compared to systems using a relatively high resistance. In this example, monitoring device 100 may use second working electrode 408 and reference electrode 406 to determine the OCP signal using the relatively "high" resistance between second working electrode 408 and both counter electrode 402 and reference electrode 406, which may help to increase an accuracy of the OCP signal compared to systems using a relatively low resistance.

Monitoring device 100 may be configured to operate first working electrode 404 only in the low-impedance mode. For instance, monitoring device 100 may be configured to provide a voltage at first working electrode 404 with a low resistance connection to counter electrode 402 that is not switchable. In some examples, monitoring device 100 may be configured to operate second working electrode 408 only in the high-impedance mode. For instance, monitoring device 100 may be configured to measure a voltage at second working electrode 408 with a high resistance connection to counter electrode 402 and reference electrode 406 that is not switchable.

Monitoring device 100 may be configured to configured to "toggle" second working electrode 408 to operate in the high-impedance mode or the low-impedance mode. For example, monitoring device 100 may be configured to operate second working electrode 408 in the low-impedance mode. When second working electrode 408 is operating in the low-impedance mode, the resistance between second working electrode 408 and counter electrode 402 may be less than the first threshold value.

Similarly, monitoring device 100 may be configured to configured to "toggle" first working electrode 404 to operate in the high-impedance mode or the low-impedance mode. For example, monitoring device 100 may be configured to operate first working electrode 404 in the high-impedance mode. For instance, when first working electrode 404 is operating in the high-impedance mode, the resistance between first working electrode 404 and both counter electrode 402 and reference electrode 406 may be greater than the second threshold value.

Monitoring device 100 may be configured to configured to "toggle" a mode for both first working electrode 404 and second working electrode 408. For example, monitoring device 100 may determine a first sensor signal based on current flowing between first working electrode 404 and counter electrode 402. In this example, monitoring device 100 may determine a first OCP signal based on a voltage across second working electrode 408 and reference electrode 406. Monitoring device 100 may determine a first glucose level of patient 112 based on the first sensor signal and the OCP signal. In this example, after determining the first sensor signal, monitoring device 100 may determine a second sensor signal based on current flowing between second working electrode 408 and counter electrode 402. Monitoring device 100 may determine, after determining the first OCP signal, a second OCP signal based on a voltage across first working electrode 404 and reference electrode 406. Monitoring device 100 may determine, a second glucose level of the patient based on the second sensor signal and the second OCP signal.

Figure 5:
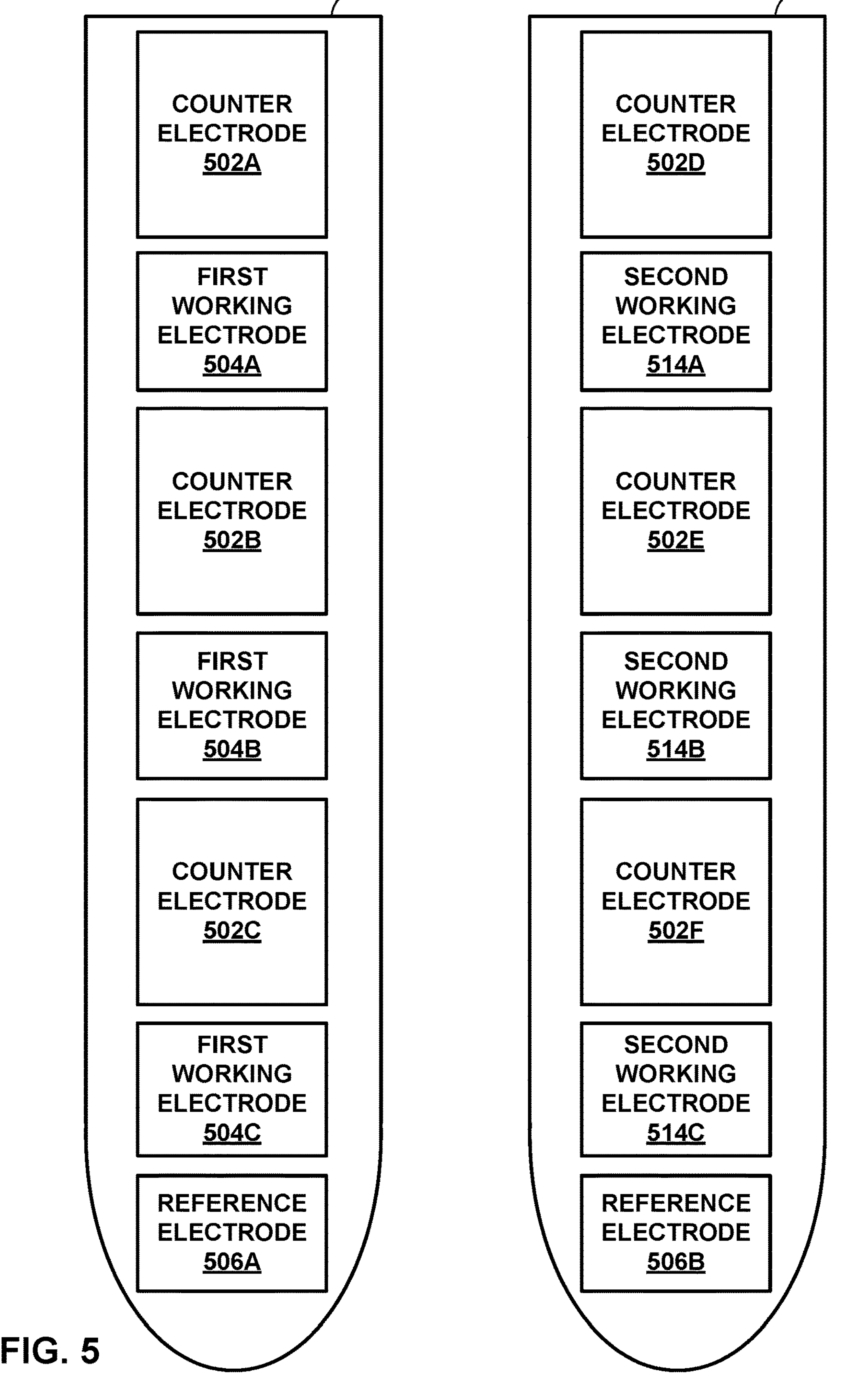
FIG. 5 is a block diagram illustrating a first example of dual sensor flexes in accordance with one or more examples described in this disclosure.

FIG. 5 is a block diagram illustrating an example of dual sensor flexes in accordance with one or more examples described in this disclosure. In some examples sensor flexes 501 and 511 may represent dual implantable sensor flexes.

In the example of FIG. 5, first working electrodes 504A-504C (collectively, referred to herein as working electrode 504) may be arranged on first implantable sensor flex 501 and second working electrodes 514A-514C may be arranged on second implantable sensor flex 511 that is different from the first implantable sensor flex. In the example of FIG. 5, counter electrodes 502A-502F may be electrically coupled to form counter electrode 502. Reference electrodes 506A, 506B may be electrically coupled to form reference electrode 506. One or more electrodes of FIG. 5 may be omitted. In some examples, an order and/or number of electrodes on each of sensor flexes 501, 511 may be different.

In the example of FIG. 5, monitoring device 100 may determine a sensor signal based on current flowing between first working electrode 504 arranged on sensor flex 501 and counter electrode 502. Monitoring device 100 may determine an OCP signal based on a voltage across second working electrode 514 arranged on sensor flex 511 and reference electrode 506.

Figure 6:
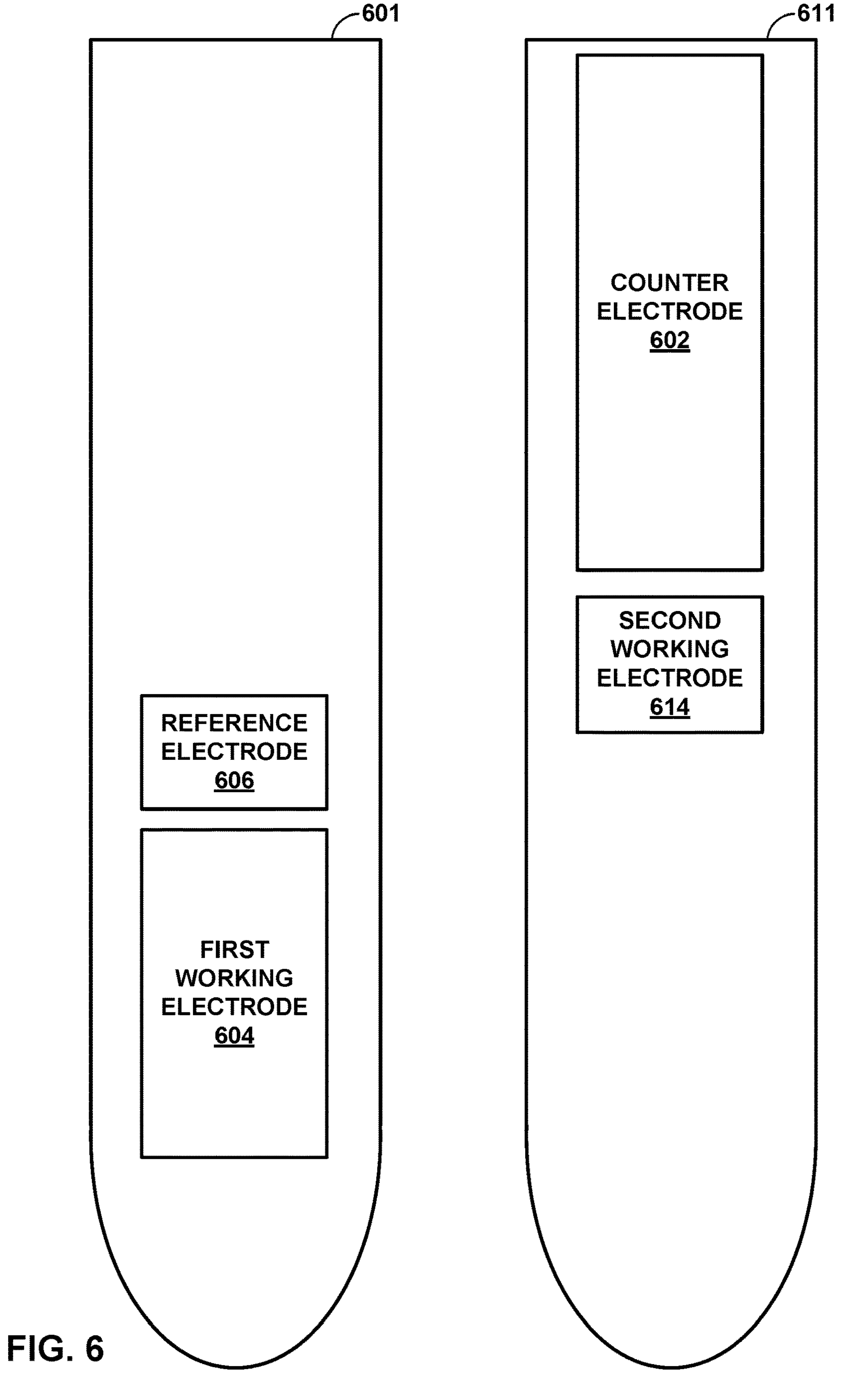
FIG. 6 is a block diagram illustrating a second example of dual sensor flexes in accordance with one or more examples described in this disclosure.

FIG. 6 is a block diagram illustrating a second example of dual sensor flexes in accordance with one or more examples described in this disclosure. In the example of FIG. 6, monitoring device 100 may determine a sensor signal based on current flowing between first working electrode 604 arranged on sensor flex 601 and counter electrode 602 arranged on sensor flex 611. Monitoring device 100 may determine an OCP signal based on a voltage across second working electrode 614 arranged on sensor flex 611 and reference electrode 606 arranged on sensor flex 601.

Figure 7:
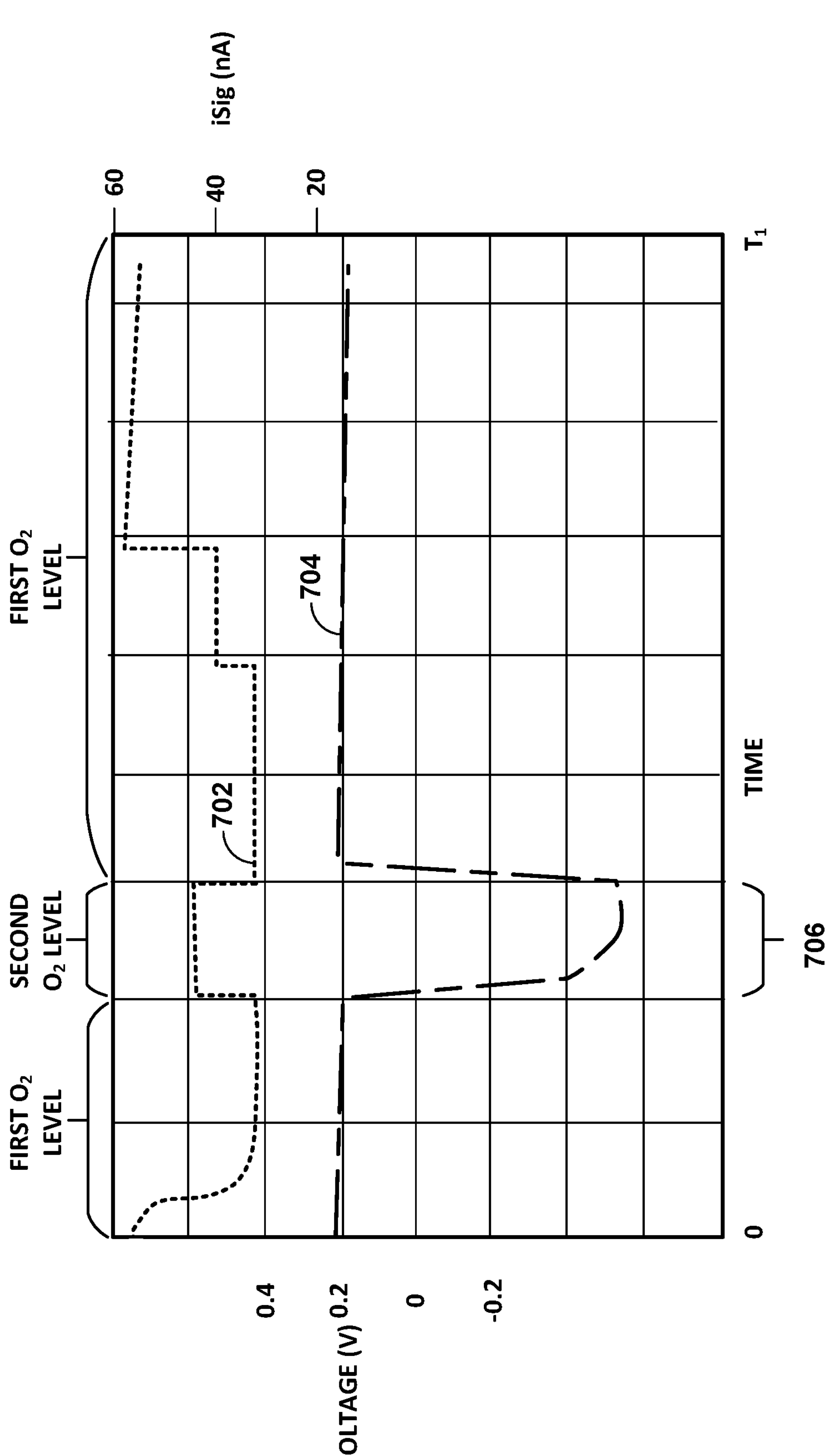
FIG. 7 is a conceptual diagram illustrating examples of a sensor signal and an open circuit potential (OCP) signal in accordance with one or more examples described in this disclosure.

FIG. 7 is a conceptual diagram illustrating examples of a sensor signal 702 and an OCP signal 704 in accordance with one or more examples described in this disclosure. The abscissa axis of FIG. 7 represents time from zero to a time value ("Ti"). The ordinate axis of FIG. 7 represents a sensor signal 702 (e.g., iSig) in nano amperes (nA) from 20 nA to 60 nA and an OCP signal 704 in volts (V) from −1.2 volts to 0.4 volts.

In the example of FIG. 7, monitoring device 100 may determine, at a first oxygen level ("first $O_2$ level"), sensor signal 702 based on current flowing between a first working electrode (e.g., first working electrode 404 of FIG. 4 or first working electrode 504 of FIG. 5) and a counter electrode (e.g., counter electrode 402 of FIG. 4, counter electrode 504 of FIG. 5, or counter electrode 604 of FIG. 6). In this example, monitoring device 100 may determine, at the first oxygen level, OCP signal 704 based on a voltage across a second working electrode (e.g., second working electrode 408 of FIG. 4 or second working electrode 508 of FIG. 5)

and a reference electrode (e.g., reference electrode 406 of FIG. 4, reference electrode 506 of FIG. 5, or reference electrode 606 of FIG. 6).

Monitoring device 100 may determine, at a second oxygen level ("second $O_2$ level"), sensor signal 702 based on current flowing between the first working electrode and the counter electrode. In this example, monitoring device 100 may determine, at the second oxygen level, OCP signal 704 based on a voltage across a second working electrode and a reference electrode. As shown, the second oxygen level may cause sensor signal 702 to increase and may cause OCP signal 704 to decrease. In accordance with the techniques of the disclosure, monitoring device 100 may account for the change (e.g., an increase or decrease) in sensor signal 702 using OCP signal 704. For instance, monitoring device 100 may determine a multiplication factor based on OCP signal 704 and multiply the multiplication factor with sensor signal 702 to determine a glucose level for patient 112. In some examples, monitoring device 100 may calculate Equation 2.

$$iSig_{Corrected} = iSig_{Raw} * \left[Const_A * \frac{OCP_{Reading}}{OCP_{Mean}} + Const_B\right] \quad \text{EQUATION 2}$$

where $iSig_{Corrected}$ is a corrected sensor value, $iSig_{Raw}$ is sensor signal 702 as measured, $Const_A$ is a first constant (e.g., preconfigured or determined by monitoring device 100), $Const_B$ is a second constant (e.g., preconfigured or determined by monitoring device 100), $OCP_{Reading}$ is OCP signal 704, and $OCP_{Mean}$ is a mean of OCP values at an oxygen level (e.g., first oxygen level).

For example, monitoring device 100 may, to determine $iSig_{Raw}$, measure current flowing between the first working electrode and the counter electrode at a time range 706. In this example, monitoring device 100 may, to determine $OCP_{Reading}$, measure a voltage across the second working electrode and the reference electrode during the time range 702. In this example, monitoring device 100 may calculate $iSig_{Corrected}$ using Equation 2. Monitoring device 100 may determine a glucose level (e.g., a blood glucose level) for patient 112 based on the $iSig_{Corrected}$. In this way, monitoring device 100 may be calibrated to help to account for a change in oxygen level from first oxygen level to second oxygen level in the tissue of patient 112, which may improve an accuracy of the monitoring device 100.

Monitoring device 100 may be configured to determine an oxygen level for patient 112 based on OCP signal 704. For example, in response to a decrease in OCP signal 704, monitoring device 100 may determine that the oxygen level for patient 112 has increased. Similarly, in response to an increase in OCP signal 704, monitoring device 100 may determine that the oxygen level for patient 112 has decreased.

Figure 8:
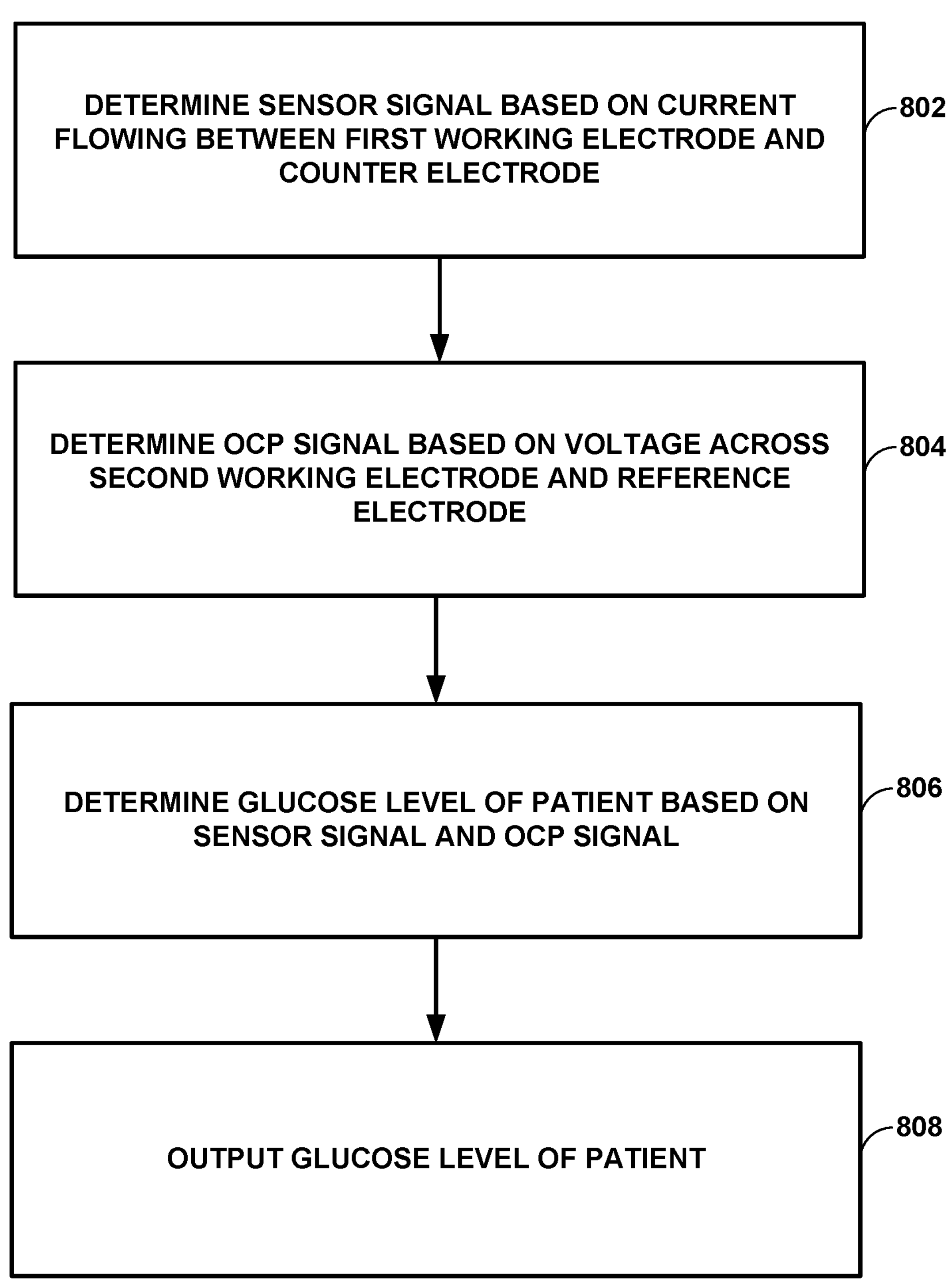
FIG. 8 is a flowchart illustrating an example technique of the disclosure.

FIG. 8 is a flowchart illustrating an example technique of the disclosure. While the example of FIG. 8 refers to the single implantable sensor flex 401 of FIG. 4, monitoring device 100 may be configured to use other types of sensor flexes and/or other numbers of sensor flexes. For example, monitoring device 100 may be configured to use two or more implantable sensor flexes.

In the example of FIG. 8, monitoring device 100 may determine a sensor signal based on current flowing between the first working electrode and the counter electrode (802). For example, monitoring device 100 may determine sensor signal 702 of FIG. 7 based on current flowing between first working electrode 404 and counter electrode 402. Monitoring device 100 may be configured to operate first working electrode 404 in a low-impedance mode. When first working electrode 404 is operating in the low-impedance mode, a resistance between first working electrode 404 and counter electrode 402 may be less than a first threshold value.

Monitoring device 100 may determine an OCP signal based on a voltage across the second working electrode and the reference electrode (804). For example, monitoring device 100 may determine OCP signal 704 of FIG. 7 based on a voltage across second working electrode 408 and reference electrode 402. Monitoring device 100 may be configured to operate second working electrode 408 in a high-impedance mode. When operating second working electrode 408 in the high-impedance mode, a resistance between second working electrode 408 and both counter electrode 402 and reference electrode 406 may be greater than a second threshold value. The second threshold value may be greater than the first threshold value.

In some examples, monitoring device 100 may be configured to toggle between operating second working electrode 408 in a low-impedance mode and a high impedance mode. When second working electrode 408 is operating in the low-impedance mode, the resistance between second working electrode 408 and counter electrode 402 may be less than a first threshold value. When second working electrode 408 is operating in the high-impedance mode, a resistance between second working electrode 408 and both counter electrode 402 and reference electrode 406 may be greater than a second threshold value.

Monitoring device 100 may determine the glucose level of the patient based on the sensor signal and the OCP signal (806). For example, monitoring device 100 may calculate Equation 2. In some examples, monitoring device 100 may output an indication of the sensor signal and the OCP signal and another device (e.g., patient device 124 or a cloud) determines the glucose level of the patient. In some examples, monitoring device 100 may determine an oxygen level for patient 112 based on the OCP signal.

Monitoring device 100 may output an indication of the glucose level (808). For example, monitoring device 100 may output an instruction to insulin pump 114, for instance, to provide therapy to patient 112. In some examples, monitoring device 100 may output an indication of the glucose level to patient device 124. Patient device 124 may display the glucose level. For instance, patient device 124 may display the glucose level and patient 112 or caretaker may dispense insulin to patient 112 (e.g., when insulin pump 114 is omitted or bypassed).

Other illustrative examples of the disclosure are described below.

Example 1. A device for determining a glucose level of a patient, the device comprising: a set of electrodes comprising a first working electrode, a second working electrode, a counter electrode, and a reference electrode, wherein the reference electrode is electrically coupled to the counter electrode; a memory; and one or more processors implemented in circuitry and in communication with the memory, the one or more processors configured to: determine a sensor signal based on current flowing between the first working electrode and the counter electrode; determine an open circuit potential (OCP) signal based on a voltage across the second working electrode and the reference electrode; determine the glucose level of the patient based on the sensor signal and the OCP signal; and output an indication of the glucose level.

Example 2. The device of example 1, wherein, to output the indication of the glucose level, the one or more processors are configured to output an instruction to an insulin pump.

Example 3. The device of example 1, wherein, to output the indication of the glucose level, the one or more processors are configured to output an indication of the glucose level to a patient device.

Example 4. The device of example 3, wherein the patient device is configured to display the glucose level.

Example 5. The device of examples 1-4, wherein the first working electrode, second working electrode, counter electrode, and reference electrode are arranged on a single implantable sensor flex.

Example 6. The device of examples 1-4, wherein the first working electrode is arranged on a first implantable sensor flex and the second working electrode is arranged on a second implantable sensor flex that is different from the first implantable sensor flex.

Example 7. The device of examples 1-6, wherein the device is configured to operate the first working electrode in a low-impedance mode, wherein, when the first working electrode is operating in the low-impedance mode, a resistance between the first working electrode and the counter electrode is less than a first threshold value; and wherein the device is configured to operate the second working electrode in a high-impedance mode, wherein, when the second working electrode is operating in the high-impedance mode, a resistance between the second working electrode and both the counter electrode and the reference electrode is greater than a second threshold value, wherein the second threshold value is greater than the first threshold value.

Example 8. The device of example 7, wherein the device is configured to only operate the first working electrode in the low-impedance mode; and wherein the device is configured to only the second working electrode in the high-impedance mode.

Example 9. The device of example 7, wherein the device is further configured to operate the second working electrode in the low-impedance mode, wherein, when the second working electrode is operating in the low-impedance mode, the resistance between the second working electrode and the counter electrode is less than the first threshold value.

Example 10. The device of examples 1-6, wherein the glucose level is a first glucose level, the sensor signal is a first sensor signal, and the OCP signal is a fist OCP signal, wherein the one or more processors are further configured to: determine, after determining the first sensor signal, a second sensor signal based on current flowing between the second working electrode and the counter electrode; determine, after determining the first OCP signal, a second OCP signal based on a voltage across the first working electrode and the reference electrode; determine, a second glucose level of the patient based on the second sensor signal and the second OCP signal; and output an indication of the second glucose level.

Example 11. The device of examples 1-10, wherein, to determine the glucose level of the patient, the one or more processors are configured to: determine a multiplication factor based on the OCP signal; and multiply the multiplication factor with the sensor signal.

Example 12. The device of examples 1-11, wherein, to determine the sensor signal, the one or more processors are configured to measure the current flowing between the first working electrode and the counter electrode during a time range; and wherein, to determine the OCP signal, the one or more processors are configured to measure the voltage across the second working electrode and the reference electrode during the time range.

Example 13. The device of examples 1-12, wherein the one or more processors are further configured to determine an oxygen level for the patient based on the OCP signal.

Example 14. A method for determining a glucose level of a patient, the method comprising: determining, with one or more processors, a sensor signal based on current flowing between a first working electrode and a counter electrode; determining, with one or more processors, an open circuit potential (OCP) signal based on a voltage across a second working electrode and a reference electrode, wherein the reference electrode is electrically coupled to the counter electrode; determining, with the one or more processors, the glucose level of the patient based on the sensor signal and the OCP signal; and outputting, with the one or more processors, an indication of the glucose level.

Example 15. The method of example 14, wherein outputting the indication of the glucose level comprises outputting an instruction to an insulin pump.

Example 16. The method of example 14, wherein outputting the indication of the glucose level comprises outputting an indication of the glucose level to a patient device.

Example 17. The method of example 16, wherein the patient device is configured to display the glucose level.

Example 18. The method of examples 14-17, wherein the first working electrode, second working electrode, counter electrode, and reference electrode are arranged on a single implantable sensor flex.

Example 19. The method of examples 14-17, wherein the first working electrode is arranged on a first implantable sensor flex and the second working electrode is arranged on a second implantable sensor flex that is different from the first implantable sensor flex.

Example 20. A non-transitory computer-readable storage medium having stored thereon instructions that, when executed, configure one or more processors to: determine a sensor signal based on current flowing between a first working electrode and a counter electrode; determine an open circuit potential (OCP) signal based on a voltage across a second working electrode and a reference electrode, wherein the reference electrode is electrically coupled to the counter electrode; determine the glucose level of the patient based on the sensor signal and the OCP signal; and output an indication of the glucose level.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable medium may cause a programmable processor, or other processor, to perform the method, e.g., when the instructions are executed. Computer-readable media may include non-transitory computer-readable storage media and transient communication media. Computer readable storage media, which is tangible and non-transitory, may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer-readable storage media. It should be understood that the term "computer-readable storage media" refers to physical storage media, and not signals, carrier waves, or other transient media.

Various examples have been described. These and other examples are within the scope of the following claims.

What is claimed is:

1. A device for determining a glucose level of a patient, the device comprising:

a set of electrodes comprising a first working electrode, a second working electrode, a counter electrode, and a reference electrode, wherein the reference electrode is electrically coupled to the counter electrode, and wherein the first working electrode is arranged on a first implantable sensor flex and the second working electrode is arranged on a second implantable sensor flex that is different from the first implantable sensor flex;

a memory; and one or more processors implemented in circuitry and in communication with the memory, the one or more processors configured to:

determine a sensor signal based on current flowing between the first working electrode and the counter electrode;

cause the second working electrode to transition to an open circuit potential (OCP) measurement mode by causing a resistance between the second working electrode and the reference electrode to be greater than a resistance between the first working electrode and the counter electrode and to be greater than a threshold value that enables measurement of an OCP signal by either disconnecting the counter electrode while the first working electrode is in a first mode for measuring the sensor signal indicative of the glucose level of the patient or by switching a resistor in to a path between the first working electrode and the second working electrode while the first working electrode is in the first mode for measuring the sensor signal indicative of the glucose level of the patient;

determine the OCP signal based on a voltage across the second working electrode and the reference electrode;

determine, using the device that is at least partially inserted subcutaneously, the glucose level of the patient based on the sensor signal and the OCP signal by correcting the sensor signal using a multiplication factor that compensates for a change in oxygen level of the patient indicated in the OCP signal; and cause insulin to be delivered to the patient based on the glucose level.

2. The device of claim 1, wherein, to cause the insulin to be delivered to the patient based on the glucose level, the one or more processors are configured to output an instruction to an insulin pump.

3. The device of claim 1, wherein the one or more processors are further configured to output an indication of the glucose level to a patient device.

4. The device of claim 3, wherein the patient device is configured to display the glucose level.

5. The device of claim 1, wherein at least a portion of the counter electrode is arranged on the first implantable sensor flex.

6. The device of claim 1, wherein the counter electrode is arranged on the second implantable sensor flex that is different from the first implantable sensor flex.

7. The device of claim 1, wherein the device is configured to operate the first working electrode in the first mode, wherein, when the first working electrode is operating in the first mode, the resistance between the first working electrode and the counter electrode is less than a first threshold value; and wherein the device is configured to operate the second working electrode in the OCP measurement mode, wherein, when the second working electrode is operating in the OCP measurement mode, the resistance between the second working electrode and both the counter electrode and the reference electrode is greater than a second threshold value, wherein the second threshold value is greater than the first threshold value.

8. The device of claim 7, wherein the device is further configured to operate the second working electrode in the first mode, wherein, when the second working electrode is operating in the first mode, the resistance between the second working electrode and the counter electrode is less than the first threshold value.

9. The device of claim 1, wherein the glucose level is a first glucose level, the sensor signal is a first sensor signal, and the OCP signal is a first OCP signal, wherein the one or more processors are further configured to:

determine, after determining the first sensor signal, a second sensor signal based on current flowing between the second working electrode and the counter electrode;

determine, after determining the first OCP signal, a second OCP signal based on a voltage across the first working electrode and the reference electrode;

determine, a second glucose level of the patient based on the second sensor signal and the second OCP signal; and output an indication of the second glucose level.

10. The device of claim 1, wherein, to determine the glucose level of the patient, the one or more processors are configured to:

determine the multiplication factor based on the OCP signal; and multiply the multiplication factor with the sensor signal.

11. The device of claim 1, wherein, to determine the sensor signal, the one or more processors are configured to measure the current flowing between the first working electrode and the counter electrode during a time range; and wherein, to determine the OCP signal, the one or more processors are configured to measure the voltage across the second working electrode and the reference electrode during the time range.

12. The device of claim 1, wherein the one or more processors are further configured to determine the oxygen level for the patient based on the OCP signal.

13. A method for determining a glucose level of a patient, the method comprising:

determining, with one or more processors, a sensor signal based on current flowing between a first working electrode and a counter electrode;

causing a second working electrode to transition to an open circuit potential (OCP) measurement mode by causing a resistance between the second working electrode and a reference electrode to be greater than a resistance between the first working electrode and the counter electrode and to be greater than a threshold value that enables measurement of an OCP signal, by either disconnecting the counter electrode while the first working electrode is in a first mode for measuring the sensor signal indicative of the glucose level of the patient, or by switching a resistor in to a path between the first working electrode and the second working electrode while the first working electrode is in the first mode for measuring the sensor signal indicative of the glucose level of the patient;

determining, with one or more processors, the OCP signal based on a voltage across a second working electrode and a reference electrode;

determining, with the one or more processors, the glucose level of the patient based on the sensor signal and the OCP signal by correcting the sensor signal using a multiplication factor that compensates for a change in oxygen level of the patient indicated by the OCP signal; and causing, with the one or more processors, insulin to be delivered to the patient based on the glucose level.

14. The method of claim 13, further comprising outputting an indication of the glucose level by outputting an instruction to an insulin pump, wherein the insulin pump is configured to deliver the insulin to the patient based on the glucose level.

15. The method of claim 13, further comprising outputting an indication of the glucose level to a patient device.

16. The method of claim 15, wherein the patient device is configured to display the glucose level.

17. The method of claim 13, wherein the first working electrode, second working electrode, counter electrode, and reference electrode are arranged on a single implantable sensor flex.

18. The method of claim 13, wherein the first working electrode is arranged on a first implantable sensor flex and the second working electrode is arranged on a second implantable sensor flex that is different from the first implantable sensor flex.

19. A non-transitory computer-readable storage medium having stored thereon instructions that, when executed, configure one or more processors to:

determine a sensor signal based on current flowing between a first working electrode and a counter electrode;

cause a second working electrode to transition to an open circuit potential (OCP) measurement mode by causing a resistance between the second working electrode and a reference electrode to be greater than a resistance between the first working electrode and the counter electrode and to be greater than a threshold value that enables measurement of an OCP signal, by either disconnecting the counter electrode while the first working electrode is in a first mode for measuring the sensor signal indicative of a glucose level of a patient, or by switching a resistor in to a path between the first working electrode and the second working electrode while the first working electrode is in the first mode for measuring the sensor signal indicative of the glucose level of the patient;

determine the OCP signal based on a voltage across a second working electrode and a reference electrode, wherein the reference electrode is electrically coupled to the counter electrode;

determine the glucose level of the patient based on the sensor signal and the OCP signal by correcting the sensor signal using a multiplication factor that compensates for a change in oxygen level of a patient indicated by the OCP signal; and cause insulin to be delivered to the patient based on the glucose level.

* * * * *